United States Patent [19]
Martin et al.

[11] 3,943,204

[45] Mar. 9, 1976

[54] METHOD FOR IMPROVING THE EXTRACTION PROPERTIES OF A TRIBUTYL PHOSPHATE SOLUTION

[75] Inventors: Earl C. Martin, Richland; Lester E. Bruns, Kennewick, both of Wash.

[73] Assignee: The United States of America as represented by the United States Energy Research and Development Administration, Washington, D.C.

[22] Filed: Feb. 5, 1974

[21] Appl. No.: 439,792

[52] U.S. Cl. ................. 260/990; 260/963; 260/978
[51] Int. Cl.² .......................................... C07F 9/11
[58] Field of Search ........................... 260/978, 990

[56] References Cited
UNITED STATES PATENTS

| | | | |
|---|---|---|---|
| 2,936,318 | 5/1960 | Moore | 260/990 |
| 3,708,508 | 1/1973 | Schulz | 260/990 X |
| 3,793,408 | 2/1974 | Schulz | 260/990 |

*Primary Examiner*—Richard L. Raymond
*Attorney, Agent, or Firm*—John A. Horan; Arthur A. Churm; James W. Weinberger

[57] ABSTRACT

A method for improving the extraction properties of a tributyl phosphate extractant used for reprocessing irradiated nuclear reactor fuel (Purex Process) containing degradation products of tributyl phosphate by contacting the extractant with diazomethane in a suitable solvent whereby the degradation products are esterified to triester phosphates which have extraction properties similar to those of tributyl phosphate.

2 Claims, No Drawings

METHOD FOR IMPROVING THE EXTRACTION PROPERTIES OF A TRIBUTYL PHOSPHATE SOLUTION

CONTRACTUAL ORIGIN OF THE INVENTION

The invention described herein was made in the course of, or under, a contract with the U.S. ATOMIC ENERGY COMMISSION.

BACKGROUND OF THE INVENTION

This invention relates to a method for improving the extraction properties of a solution of tributyl phosphate in an organic solvent. More specifically, this invention relates to a method for improving the extraction properties of a solution of tributyl phosphate by esterifying the chemical and radiological degradation products of tributyl phosphate which may be present therein.

As the numbers of nuclear reactors increase, the methods and techniques for reprocessing the spent fuel which has been irradiated in these reactors must also be improved. This is necessary to speed up reprocessing and to improve recovery of uranium and plutonium so that these and other reactors under construction and planned for in the future may be fueled.

A number of methods of fuel reprocessing have been developed such as halide volatility processes, pyrometallurgical processes and solvent extraction processes.

Of these processes, the solvent extraction process which utilizes tributyl phosphate (TBP) in a kerosene base is presently in wide use. This process is generally referred to as the Purex Process and is described in detail in "Reactor Handbook", Second Edition, Vol. 2, "Fuel Reprocessing", Stoller and Richards, Interscience, 1961. This process relies upon the extractability of uranyl nitrate and the relative inextractability of plutonium (III) to separate these two elements from each other and from an aqueous nitric acid feed solution.

The use of tributyl phosphate as an extractant for uranium and plutonium has had widespread acceptance in the nuclear industry for the past 25 years. This material, nevertheless, suffers from both chemical and radiological degradation when exposed to the radioactive solutions containing extractable actinides.

The presence of the degradation products such as the dibutyl phosphate (DBP), mono-butyl phosphate (MBP) and phosphoric acid has a detrimental effect upon the extraction process. Among the problems created by the presence of these materials are poor phase separation in the contractor, with subsequent losses of entrainment and/or reduced throughput, extraction of fission products along with the actinides, resulting in a loss of purity of uranium and plutonium, loss of actinides caused by the formation of nonstrippable complexes in the organic phase, and the formation of precipitates.

Thus it can be seen that the presence of degradation products seriously reduces the effectiveness of the extraction process. Techniques have been established to remove the degradation products. These include a carbonate aqueous scrub of the organic TBP solution, the use of macroreticular ion exchange resins and others. All of these techniques involve the use of extra columns for the cleanup, extra chemicals, a restoration of the cleanup system and finally the disposal of the additional radioactive waste stream. Even with the use of carbonate scrubs, periodically, the concentration of degradation products rises to a level such that the entire organic stream must be discarded. All of these treatment techniques are expensive. An ideal technique would be one that would restore the extracting solution either to its initial condition or one that closely approximates the initial solution.

SUMMARY OF THE INVENTION

We have developed a process for improving the effectiveness of the tributyl phosphate extracting solution which eliminates many of the previously enumerated problems. It has been found that, by contacting the partially degraded tributyl phosphate solution with an esterifying agent, the degradation products of tributyl phosphate can be esterified to triesters which have extraction properties similar to tributyl phosphate. Thus a method has been developed which is relatively inexpensive, free from interfering by-products and side reactions and by which the extraction system is restored to almost its original efficiency. In addition, by this method, expensive cleanup procedures are eliminated and the use-life of the extraction solution is greatly prolonged.

It is therefore one object of our invention to provide a process for improving the extraction properties of a tributyl phosphate solution.

It is a further object of this invention to improve the extraction properties of tributyl phosphate extractant solutions containing degradation products of tributyl phosphate.

Finally, it is the object of this invention to provide a method for esterifying the degradation products of tributyl phosphate to their triesters in order to improve their extraction properties.

DETAILED DESCRIPTION OF THE INVENTION

These and other objects of the invention for improving the extraction properties of degraded tributyl phosphate extractant solutions may be met by contacting the extractant solution containing the degradation products of tributyl phosphate with 0.1 M diazomethane in a suitable solvent, the quantity of diazomethane being at least equal to the quantity of degradation products present, whereby the degradation products of tributyl phosphate are esterified to triester phosphates which have improved extraction properties. The tributyl phosphate solution containing the esterified degradation products may then be recycled for further extraction of uranium and plutonium in the irradiated nuclear reactor fuel reprocessing cycle.

The esterifying agent may be any compound which will quickly and easily esterify the degradation products of tributyl phosphate without forming interfering by-products or causing any adverse side reactions while producing a triester which has extraction properties similar to tributyl phosphate. One esterifying agent which has been found to be exceptionally effective is diazomethane.

It must be remembered that diazomethane, when in a pure or highly concentrated form, is susceptible to explosive detonation by shock or by catalysis on a sharp edge or a scratch and that it is also highly toxic. However, it has been found that in concentrations of 0.1 M or less in a suitable solvent it is relatively easy to handle and no problems have been encountered. A number of solvents have been found to be suitable for diazomethane at this concentration such as, for example, ether, carbon tetrachloride and other halogenated hydrocarbons and normal paraffin hydrocarbon or NPH. NPH would be especially suitable, since it is the diluent presently in use for tributyl phosphate in the Purex Process. The NPH contains 97 w/o of $C_{10}$ to $C_{14}$ straight chain hydrocarbons having a specific gravity of 0.74 to 0.76 at 60°F. and a flash point of 155° to 160°F.

The amount of diazomethane necessary to esterify the degradation products is a quantity equal to the quantity of the degradation products present in the tributyl phosphate solution. However, in order to insure that esterification is complete, it is preferable that the amount of diazomethane be double the quantity of degradation products present. This will insure that esterification is complete even if small quantities of water, which would hydrolyze the diazomethane, are present in the organic solution. Any excess diazomethane which may remain after esterification is complete will not affect the extractability of the tributyl phosphate solution, since it will be hydrolyzed as soon as it comes in contact with any aqueous solution.

The synthesis of diazomethane in a dilute solution can be readily accomplished by dissolving N-methyl-N-nitroso-p-toluenesulfonamide to 0.1 M in diethyl ether and adding this dropwise to a solution of sodium hydroxide, water and dibutylcarbitol maintained at a temperature of 60°. The diazomethane codistills from the reaction mixture with ether so that a dilute solution is always maintained. The distillate is condensed at a cold finger and is collected in an ice-cooled receiver. Ether solutions of diazomethane can be kept for several weeks at a temperature near 0°C.

The preferred temperature for the operation of this process is ambient, since higher temperatures will cause a loss of diazomethane.

The following example is given as illustrative of the process of the invention and is not to be taken as limiting the scope or extent of the invention.

EXAMPLE

Feed solution: 1 M aluminum nitrate nonahydrate, 2 M $HNO_3$, spiked with 1 g/l Pu Extracting solution: 20% $TBP/CCl_4$ + 0.02 M DBP One half of the extracting solution was treated with diazomethane. The feed solution (20 ml) was stirred for 15 minutes with 20 ml of each of the extracting solutions. The plutonium was then removed from the organic solution by extraction with a solution composed of 0.15 M $HNO_3$ and 0.25 M hydroxylamine nitrate. The organic solution was sampled and analyzed for plutonium by alpha counting after each of these extractions. A comparison is shown in the table below for an untreated extraction solution and a diazomethane treated extracting solution. The ideal solution would be the complete absence of plutonium in the residual organic.

TABLE

| Organic Solvent | | Adjusted $c/c/\lambda$ | Pu(g/l) |
|---|---|---|---|
| Untreated | After Strip 1 | 1965 | $3.6 \times 10^{-2}$ |
| | After Strip 2 | 1925 | $3.5 \times 10^{-2}$ |
| | After Strip 3 | 1680 | $3.1 \times 10^{-2}$ |
| Diazomethane Treated | After Strip 1 | 10.3 | $18.9 \times 10^{-5}$ |
| | After Strip 2 | 1.2 | $2.2 \times 10^{-5}$ |
| | After Strip 3 | 1.2 | $2.2 \times 10^{-5}$ |
| (Background 0.1 C/M) | | | |

In this instance, the improvement was better than 1400-fold. Other experiments have been performed with similar results verifying the fact that a substantial improvement in plutonium stripping can be made by the addition of diazomethane to degraded solvent. Although in this example the TBP was dissolved in $CCl_4$ rather than in the NPH of the Purex Process, this will have no effect upon the esterification of the degradation products by the diazomethane.

The process of the invention can easily and readily be incorporated into the Purex Process stream after plutonium has been stripped from the extractant. A solution of diazomethane could continuously be added to the spent TBP extractant solution in place of a scrubbing step before it is recycled to extract uranium and plutonium from the acid feed solution.

As can be seen from the above example, the addition of diazomethane to tributyl phosphate solution greatly improves the extractability of the solution and provides a simple, effective method for improving the extraction properties of a degraded tributyl phosphate solution.

It is to be understood that the method of this invention is not to be limited to the details given herein but that it may be modified within the scope of the appended claims.

The embodiments of the invention in which an exclusive property or privilege is claimed are defined as follows:

1. A process for improving the extraction properties of tributyl phosphate in an organic diluent selected from the group consisting of kerosene, carbon tetrachloride and normal paraffin hydrocarbon containing dibutyl phosphate, monobutyl phosphate and phosphoric acid as degradation products of tributyl phosphate comprising: contacting the tributyl phosphate solution containing the degradation products with an amount of diazomethane effective to esterify the degradation products, the diazomethane being present up to 0.1 M in a solvent selected from the group consisting of ether, halogenated hydrocarbons, and normal paraffin hydrocarbons, whereby the degradation products are esterified to the triesters which have improved extraction properties.

2. The process of claim 1 wherein the quantity of diazomethane is equal to double the quantity of degradation products present in the tributyl phosphate solution.

* * * * *